United States Patent [19]

Cliffe

[11] Patent Number: 5,082,843

[45] Date of Patent: Jan. 21, 1992

[54] PYRAZINYL AND PYRIDAZINYL ETHERS

[75] Inventor: Ian A. Cliffe, Cippenham, England

[73] Assignee: John Wyeth and Brother Limited, Maidenhead, England

[21] Appl. No.: 606,005

[22] Filed: Oct. 30, 1990

Related U.S. Application Data

[62] Division of Ser. No. 497,273, Mar. 22, 1990, Pat. No. 4,997,839, which is a division of Ser. No. 226,657, Aug. 1, 1988, Pat. No. 4,929,625.

[30] Foreign Application Priority Data

| Aug. 4, 1987 [GB] | United Kingdom | 8718444 |
| May 20, 1988 [GB] | United Kingdom | 8811975 |

[51] Int. Cl.⁵ .................. C07D 453/02; A61K 31/46
[52] U.S. Cl. .................. 514/253; 544/238; 544/408
[58] Field of Search .................. 514/253; 544/408, 238

[56] References Cited

U.S. PATENT DOCUMENTS

| 2,640,829 | 6/1953 | Wilson et al. | 546/126 |
| 3,716,544 | 2/1973 | Gadient | 546/126 |
| 4,533,498 | 8/1985 | Blaney et al. | 544/319 |
| 4,643,995 | 2/1987 | Engel et al. | 514/304 |
| 4,766,215 | 8/1988 | Abou-Gharbia | 544/408 |
| 4,843,074 | 6/1989 | Rzeszotarski | 514/253 |

FOREIGN PATENT DOCUMENTS

| 0201165 | 11/1986 | European Pat. Off. |
| 0278173 | 8/1988 | European Pat. Off. |
| 2125398 | 3/1984 | United Kingdom |
| 2152048 | 7/1985 | United Kingdom |

OTHER PUBLICATIONS

Chem. Abstr., 57 9805c (1962).
Richardson, B. P. et al., Nature, 316, 126–131 (1985).

*Primary Examiner*—Donald G. Daus
*Attorney, Agent, or Firm*—Arthur G. Seifert

[57] ABSTRACT

Novel ethers of formula

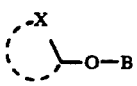
(I)

their heteroaromatic N-oxides, and the pharmaceutically acceptable acid additions of the compounds of formula (I) and their N-oxides possess 5-HT$_3$-antagonistic activity. In the formula

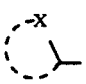

represents an optionally substituted heteroaryl group containing a hetero atom X and -B represents a saturated azabicyclic ring such as quinuclidyl or tropanyl.

12 Claims, No Drawings

PYRAZINYL AND PYRIDAZINYL ETHERS

This application is a divisional of application Ser. No. 07/497,273, filed on Mar. 22, 1990, now U.S. Pat. No. 4,997,839, issued on Mar. 5, 1991, which, in turn, is a divisional of application Ser. No. 07/226,657, filed on Aug. 1, 1988, now U.S. Pat. No. 4,929,625, issued on May 29, 1990.

This invention relates to ethers. In particular the invention relates to novel ethers, to processes for their preparation, their use and to pharmaceutical compositions containing them. The ethers are useful as antagonists of specific 5-hydroxytryptamine (5-HT) receptors as explained hereinbelow.

The novel ethers of the present invention are compounds of the general formula (I)

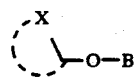

the heteroaromatic N-oxides of the compounds in which X is nitrogen; and the pharmaceutically acceptable acid addition salts of the compounds of formula I or the N-oxides, wherein

represents an optionally substituted heteroaryl group containing at least one hetero atom X selected from the group consisting of nitrogen, oxygen and sulphur; -B represents a saturated azabicyclic ring comprising from 7 to 11 ring carbon atoms and a ring nitrogen atom which is separated from the O atom of the ether linkage by 2 or 3 ring carbon atoms and where the ring nitrogen atom is not in the bridgehead position the N may be unsubstituted or substituted by a group $R^1$ where $R^1$ is $C_{1-6}$-alkyl, $C_{3-5}$-alkenyl, $C_{3-6}$-cycloalkyl, $C_{3-6}$-cycloalkyl-$C_{1-2}$alkyl or aryl- or heteroaryl-$C_{1-2}$-alkyl (where the aryl group is a phenyl or naphthyl radical optionally substituted by one or more halogen, $C_{1-4}$-alkoxy or $C_{1-4}$-alkyl groups and the heteroaryl group is a mono- or bicyclic heteroaryl radical containing one or two hetero atoms selected from oxygen, nitrogen and sulphur); and the -OB moiety is ortho to the hetero atom X; with the proviso that when B represents a quinuclidyl or a tropanyl radical,

is other than a substituted or unsubstituted 2-pyridyl radical.

Compounds of formula I in which

represents 2-pyridyl optionally substituted by specified substituents and B represents a quinuclidyl or tropanyl radical are disclosed generically, and compounds in which

represents 6-chloropyrid-2-yl- and B represents tropan-3-yl or quinuclidyl are disclosed specifically, in GB 2152048A. The compounds are stated to have analgesic activity. The publication does not disclose 5-HT$_3$-antagonistic activity for the compounds. The compounds are excluded from the above scope Examples of heterocycles from which the heteroaryl radical

is derived include 5 membered heterocycles with one hetero atom (e.g. furan, pyrrole and thiophene) which may be ring fused to, for example, a benzene or cyclohexane ring (e.g. benzo(b)furan, benzo(c)furan, indole, benzothiophene); 5-membered heterocycles having two heteroatoms in 1,2 or 1,3-positions which may be ring fused to other rings (e.g. oxazoles, pyrazoles, imidazoles, thiazoles, benzimidazoles, benzoxazoles, purines); 5-membered heterocycles with three heteroatoms which may be ring fused to other rings (e.g. triazoles, benzotriazoles, oxadiazoles); 6-membered heterocycles with one heteroatom and which may be ring fused to other rings (e.g. pyridine, quinoline, isoquinoline, phenanthrine, 5,6-cycloheptenopyridine, 5,6-cyclohexeneopyridine); 6-membered heterocycles with two heteroaatoms which may be ring fused to other rings (e.g. pyridazines, cinnolines, phthalazines, pyrazines, quinoxalines, pyrimidines, quinazolines); 6-membered heterocycles with three heteroatoms (e.g. 1,3,5-triazine) 7-membered heterocycles which may be fused to other rings (e.g. diazepines, benzodiazepines). In each example the heterocycles may optionally be substituted by, for example, $C_{1-4}$alkyl, $C_{1-4}$alkoxy, amino, $C_{1-4}$alkylamino, di($C_{1-4}$-alkyl)amino, halogen (preferably fluorine or chlorine), trifluoromethyl, phenyl, halophenyl, $C_{1-4}$ alkylphenyl, $C_{1-4}$-alkoxy phenyl, carboxy, carboxamido, nitro, thiol, $C_{1-4}$-alkylthio, $C_{1-4}$-alkoxycarbonyl. Preferred groups include 2-pyridyl optionally substituted by, for example, chloro, nitro, $C_{1-4}$-alkyl or carboxamido; 2- or 4- pyrimidyl optionally substituted by for example chloro, amino, $C_{1-4}$-alkoxy; 2-pyrazinyl optionally substituted by, for example, halo or $C_{1-4}$-alkyl; 2-pyridazinyl optionally substituted by, for example, halo or $C_{1-4}$-alkoxy; 2-quinolyl or 1- isoquinolyl optionally subsituted by $C_{1-4}$-alkyl; 2-thienyl; 2-benzo(b)thienyl; 1H-indazol-3-yl optionally substituted by, for example, nitro or $C_{1-4}$-alkyl; 2-benzoxazolyl; 2-benzothiazolyl; and 6-phenanthrinyl.

Particularly preferred groups are optionally substituted pyridazines and also the bicyclic groups specifically mentioned above.

Examples of the saturated azabicyclic ring B include groups of the following formulae

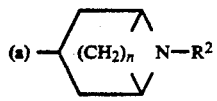     (II)

where n is 2,3 or 4 and $R^2$ is hydrogen or has the meaning given for $R^1$ above

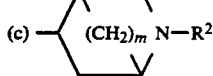     (III)

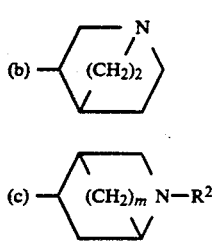     (IV)

where $R^2$ has the meaning given above and m is 1, 2 or 3 and

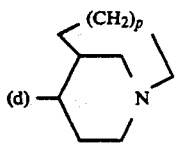     (V)

where p is 0, 1 or 2.

The preferred group B is that of formula (II) particularly that in which n is 2 and that in which $R^2$ is $C_{1-4}$-alkyl, preferably methyl. The radical in which n is 2 and $R^2$ is methyl is known as tropan-3-yl.

The radical of formula (III) is known as quinuclidyl.

In the radical of formula (IV), preferably m is 2, and $R^2$ is preferably $C_{1-4}$-alkyl, particularly methyl.

In the radical of formula (V), p is preferably 1.

The groups of formulae (II) to (IV) may contain at least one asymmetric carbon atom so that the compounds of the invention can exist in different stereoisomeric forms. The compounds can, for example, exist as racemates or optically active forms. Furthermore radicals such as those of formulae (II) to (IV) can exist in two different configurations corresponding to the endo configuration as in tropine and the exo configuration as in pseudotropine. The endo configuration is preferred.

In the compounds of formula I, any alkyl group is preferably methyl, ethyl, propyl, or butyl; any alkoxy group is preferably methoxy, ethoxy or propoxy; an alkenyl group is preferably allyl or methallyl; a cycloalkyl is preferably cyclopentyl or cyclohexyl; cycloalkylalkyl is preferably cyclopentylmethyl or cyclohexylmethyl; arylalkyl is preferably benzyl; and where the $R^1$ group contains a heteroaryl radical this may be any one of the heteroaryl groups mentioned above in connection with the

radical.

The compounds of the invention may be prepared by methods known for the preparation of ethers. For example, a compound of formula

     (VI)

or a N-oxide thereof may be condensed with a compound of formula $$Z^1\text{-B} \qquad (VII)$$

where

and B are as defined above and one of Z and $Z^1$ is hydroxy and the other is a leaving group such as halogen, $C_{1-6}$-alkylsulphonyloxy (e.g. methylsulphonyloxy) or arylsulphonyloxy where the aryl radical may be, for example, phenyl or naphthyl optionally substituted by $C_{1-4}$-alkyl (e.g. p-toluenesulphonyloxy). Preferably Z is a leaving group, particularly halogen, and $Z^1$ is hydroxy. The condensation may be carried out in presence of a condensing agent, particularly a basic condensing agent such as an alkali metal or alkaline earth metal hydroxide or carbonate, potassium or sodium hydride, phenyl- or an alkyl-lithium (e.g., butyllithium), an alkali metal amide (e.g., lithium diisopropylamide) or an organic base such as a tertiary amine, pyridine or piperidine. The condensation may be carried out in an organic solvent. The anion of the alcohol may be first prepared by reaction of the alcohol with a strong base and the anion may be subsequently be reacted with the second reactant containing the leaving group.

It will be realised that if either the reactant (VI) or (VII) contains groups that would be affected under the reaction conditions employed for the condensation reaction the group may be protected and the protecting group subsequently removed. For example hydroxy groups may be protected by formation of acetals or ethers (e.g., benzyl or silyl ethers) and amino groups may be protected by formation of urethanes or N-benzyl derivatives.

In addition, any substituent present in the final compound of formula (I) may be removed or replaced by another substituent using methods that are known in the art. For example a chloro substituent on the heteroaromatic ring may be removed by catalytic hydrogenation or an alkoxycarbonyl substituent may be reduced to hydroxymethyl.

The compounds of formula (I) in which X is nitrogen may be converted into their heteroaromatic N-oxides by methods known for analogous compounds. For example, the compounds of formula (I) may be oxidised e.g. in an inert solvent with a peracid (e.g. peracetic acid, perbenzoic acid or m-chloroperbenzic acid), hydrogen peroxide, an alkali metal peroxide or an alkyl peroxide. Oxidation may give the di-oxide which may be subsequently reduced, e.g., with sulphur di-oxide, to the mono N-oxide of the nitrogen containing heteroaromatic ring.

The starting materials of formulae (VI) and (VII) are described in the literature or may be prepared by methods known for analogous compounds.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids. The compounds of the present invention possess pharmacological activity. In particular they antagonise specific 5-hydroxytryptamine (5-HT) receptors in warm blooded animals. Specifically the compounds possess $5-HT_3$ antagonistic activity and hence are of value in conditions where antagonism of $5-HT_3$ receptors is desirable. $5-HT_3$-antagonists are also termed "antagonists of 'neuronal' 5-hydroxytryptamine receptors" and "serotonin (5-hydroxytryptamine) M-receptor antagonists". Such compounds have been described as being useful inter alia in the treatment of migraine, emesis, anxiety, gastro-intestinal disorders and as anti-psychotics.

The compound of the invention are tested for $5-HT_3$ receptor antagonism in the isolated vagus nerve of the rat by a method based upon that of Ireland S. J. and Tyers M. B., Brit. J. Pharmacol., 1987, 90, 229–238. The procedure relies upon the ability of 5-HT to induce depolarization of neurones in the cervical vagus nerve by a direct action on $5-HT_3$ receptors. A concentration-response curve to 5-HT induced depolarization is obtained and the antagonists are added to the bath containing the isolated nerve before repeating the 5-HT concentration-response curve. Antagonist potency is estimated for the 5-HT concentration ratios and expressed as an apparent $pK_B$ value (where $K_B$ is the antagonist dissociation constant). When tested by this procedure endo-8-methyl-3-(2-quinolyloxy)-8-azabicyclo[3.2.1]octane, a representative compound of this invention, had a $pK_B$ of 7.5.

The compounds of the invention are also tested for $5-HT_3$ antagonistic activity in the isolated right atrium of the rabbit heart based upon the method of Fozard J. R., Naunyn-Schmiedeberg's Arch. Pharmacol., 1984, 326, 36–44. This procedure relies upon the ability of 5-HT to stimulate $5-HT_3$ receptors present on sympathetic nerve terminals in the heart, causing release of noradrenaline which evokes an increase in the spontaneous rate of beating. The antagonist potency is expressed in a similar manner to that of the preceding test method i.e. as an apparent $pK_B$. When tested by this procedure endo-8-methyl-3-(2-quinolyloxy)-8-azabicyclo[3.2.1]octane, a representative compound of this invention, had a $pK_B$ of 8.6.

The invention further provides a compound of formula (I) or its heteroaromatic N-oxide or a pharmaceutically acceptable acid addition salt thereof for use in antagonising $5-HT_3$ receptors in a mammal.

The invention also provides a pharmaceutical composition comprising a compound of the invention in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g., glycerol and glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise a compound of the invention in a liquid carrier; such compositions may be administered for example in the form of a spray or as drops. The liquid carrier may be water (which may contain further components to provide the desired isotonicity and viscosity of the composition). The composition may also contain additional excipients such as preservatives, surface-active agents and the like. The compositions may be contained in a nasal applicator that enables the composition to be administered as drops or as a spray. For administration from an aerosol container the composition should also include a propellant.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in packaged form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

Endo-8-methyl-3-(2-pyrimidyloxy)-8-azabicyclo[3.2.-1]octane

A stirred solution of tropine (6 g, 42.5 mmol) in dry dimethyl sulphoxide (50 ml) was treated with sodium hydride, 50% dispersion in oil (2.3 g containing ca. 47.9 mmol sodium hydride) under nitrogen. After 30 min, the solution was treated with 2-chloropyrimidine (5.2 g, 45.4 mmol), and after 3 h treated with water (200 ml) and extracted with ethyl acetate (2×100 ml). The organic phases were combined and extracted with 0.25N-HCl (200 ml). The aqueous extract was washed with ethyl acetate (2×200 ml), basified with sodium hydroxide and extracted with ethyl acetate (2×200 ml). The extracts were dried (magnesium sulphate) and evaporated in vacuo to give a yellow liquid. The liquid was converted into the hydrochloride salt with ethereal hydrogen chloride and methanol. The salt was recrystallised from ethyl acetate-methanol to give the title compound as the dihydrochloride (3.86 g), mp 205°-207° (dec.) (Found: C,48.5; H,6.7; N,14.1 $C_{12}H_{17}N_3O \cdot 2HCl$ requires C,48.6; H,6.8; N,14.2%).

EXAMPLE 2

Endo-8-methyl-3-(2-quinolyloxy)-8-aza-bicyclo[3.2.-1]octane

A stirred solution of tropine (5.94 g, 42.1 mmol) in dry dimethyl sulphoxide (40 ml) was treated with sodium hydride, 50% dispersion in oil (2.3 g containing ca. 47.9 mmol sodium hydride) under nitrogen. After 30 min the solution was treated with 2-chloroquinoline (6.88 g, 42.1 mmol), and after 3 h treated with water (200 ml). The solution was extracted with ether (3×150 ml). The extracts were combined and extracted with 0.25N-HCl (200 ml). The aqueous extract was washed with ether (200 ml), basified with 10N-NaOH, and extracted with ethyl acetate (2×200 ml). The extracts were dried (magnesium sulphate) and evaporated in vacuo to give a yellow solid which was triturated with ether (10 ml). The solid was converted into the hydrochloride salt with ethereal hydrogen chloride and methanol. The salt was recrystallised from ethyl acetate-methanol to give the title compound as the dihydrochloride (4.1 g), m.p. 190°-200° (dec). Found: C,59.3; H,6.7; N,7.85. $C_{17}H_{20}N_2O \cdot 2HCl$ requires C,59.8; H,6.5; N,8.2%).

EXAMPLE 3

Endo-8-methyl-3-(2-pyrazinyloxy)-8-azabicyclo[3.2.-1]octane

The above compound was prepared from tropine (9.09 g, 63.7 mmol), 2-chloropyrazine (7.33 g, 64.0 mmol), and sodium hydride, 50% dispersion in oil (3.4 g) using the method described in Example 1.

The dihydrochloride salt was isolated as colourless crystals (8.75 g), m.p. 244°-246° (dec) (from methanol-ethyl acetate) (Found: C,47.1; H,6.7; N,13.7. $C_{12}H_{17}N_3O \cdot 2HCl \cdot \frac{1}{2}H_2O$ requires C,47.2; H,6.8; N,13.8%).

EXAMPLE 4

Endo-3-(6-chloropyridazin-2-yloxy)-8-melhyl-8-azabicyclo[3.2.1]octane

The above compound was prepared by the method described in Example 1.

The reaction of tropine (6.0 g, 42.6 mmol), 3,6-dichloropyridazine (12.7 g, 85.2 mmol), and sodium hydride, 50% dispersion in oil (2.25 g) gave a brown solid which was purified by chromatography (alumina; ether).

The dihydrochlorise salt was isolated as colourless crystals (0.8 g), m.p. 181°-184° (dec.) (from methanol-ethyl acetate) (Found: C,43.5; H,5.6; N, 13.1. $C_{12}H_{16}ClN_3O \cdot 2HCl \cdot \frac{1}{2}H_2O$ requires C,43.5; H,5.6; N,12.7%).

EXAMPLE 5

Endo-3-(6-chloropyrazin-2-yloxy)-8-methyl-8-azabicyclo[3.2.1]octane

The compound was prepared from 2,6-dichloropyrazine (6.49 g, 43.6 mmol), tropine (5.58 g, 39.6 mmol) and sodium hydride, 50% dispersion in oil (2.1 g) by the method outlined in Example 1.

The product was converted to the hydrochloride salt and recrystallised from methanol-ethyl acetate to give the title compound as the hydrochloride (3.77 g), m.p. 275°-277° (dec.) (Found: C,49.7; H,5.8; N,14.6. $C_{12}H_{16}ClN_3O \cdot HCl$ required C,49.6; H,5.9; N,14.5%).

EXAMPLE 6

Endo-3-(benzothiazol-2-yloxy)-8-methyl-8-azabicyclo[3.2.1]octane

A stirred solution of tropine (6.10 g, 43.3 mmol) in dry dimethylsulphoxide (100 ml) was treated with sodium hydride, 50% dispersion in oil (2.3 g) under nitrogen. After 40 min, 2-chlorobenzothiazole (6.2 ml, 47.7 mmol) was added and, after 18 h, the mixture was poured into water (400 ml). The precipitate was filtered and recrystallised from ethyl acetate to give the title compound as yellow crystals. The hydrochloride salt was isolated from ethyl acetate-methanol as white crystals (7.04g) m.p. 225°-227° (dec.). (Found: C,58.2; H,6.2; N,9.0. $C_{15}H_{18}N_2OS.HCl$ requires C,58.0; H,6.2; N,9.0%).

EXAMPLE 7

Endo-3-(isoquinolin-1-yloxy)-8-methyl-8-azabicyclo[3.2.1]octane

The title compound was prepared by a process analogous to that described in Example 1 in which the 3 day reaction of tropine (5.5 g, 38.8 mmol), 1-chloroisoquinoline (6.99 g, 42.7 mmol), and sodium hydride, 50% dispersion in oil (2.05 g) gave a brown solid. This was purified by passage through Florisil using ethyl acetate as the eluant.

The one and a half hydrochloride salt was isolated as colourless crystals (7.5g) m.p. 184°-205° (dec) (from methanol-ethyl acetate). (Found: C,62.8; H,6.6; N,8.4. $C_{17}H_{20}H_2O$. 1½ HCl requires C,63.2; H,6.7; N,8.7%).

EXAMPLE 8

Endo-8-methyl-3-(isoquinolin-1-yloxy)-8-azabicyclo[3.2.1]octane Ar-mono-N-oxide

A stirred solution of the free base of the product from example 7 (1.38 g, 5.1 mmol) in dichloromethane (50 ml) was treated with m-chloroperbenzoic acid, 80-85% (2.88 g, ca 13.8 mmol). After 24 h, the solution was evaporated in vacuo and the residue purified by chromatography [alumina; chloroform-methanol (20:1)] to give endo-8-methyl-3-(isoquinolin-1-yloxy)-8-azabicyclo[3.2.1]octane di-N-oxide (0.73 g) as a mixture of diastereoisomers (60:40).

A stream of sulphur dioxide was passed through a solution of the di-N-oxide in ethanol (10 ml) at 0°. The saturated solution was warmed to room temperature and evaporated in vacuo. Ethanol (10 ml) was added and the solution re-evaporated in vacuo. The residue was dissolved in chloroform (20 ml) and the solution stirred over sodium carbonate and magnesium sulphate for 30 min, filtered, and evaporated in vacuo. The residue was purified by chromatography to give a yellow solid.

The dihydrobromide salt of the product was prepared and recrystallised from ethyl acetate-methanol to give the title compound as the dihydrobromide (0.408 g) m.p. 167°-169° (dec). (Found: C,40.8; H,5.2; N,5.5. $C_{17}H_{20}N_2O_2$ 2HBr. $3H_2O$ requires C, 40.8; H,5.6; N,5.6%).

EXAMPLE 9

Endo-3-(pyridazin-3-yloxy)-8-methyl-8-azabicyclo3.2.1]octane

A solution of endo-3-(6-chloropyridazin-2-yloxy)-8-methyl-8-azabicyclo[3.2.1]octane dihydrobromide (2.97 g, 7.3 mmol) in ethanol (250 ml) was treated with 33% w/w aqueous ammonia (50 ml), reduced with hydrogen at 50 p.s.i. using 10% palladium on charcoal (1.8 g) as catalyst, filtered, and evaporated in vacuo to dryness. The residue was azeotroped in vacuo with toluene (100 ml) and triturated with dichloromethane (200 ml). The triturates were dried (MgSO₄) and evaporated in vacuo to give a solid which was recrystallised from ethyl acetate-ethanol to give colourless crystals of the product (1.07 g). The monohydrobromide salt of the product was prepared as colourless crystals, m.p. 223°-227° (Found: C,47.6; H,6.1; N,13.8 $C_{12}H_{17}N_3O$ HBl requires C,48.0; H,6.0; N,14.0%).

EXAMPLE 10

2-Quinolinyl 3-quinuclidinyl ether

Sodium hydride, 80% dispersion in oil (1.11 g) was treated with dimethyl sulphoxide (100 ml) with stirring and iced water-bath cooling under a bubbler air-lock. 3-Quinuclodinol (4.227 g, 33.6 mmol) was added after 15 min and 2-chloroquinoline (6.05 g, 37.0 mmol) added after 45 min. The mixture was allowed to warm to room temperature and after 6 days poured into water (400 ml). The mixture was extracted with ethyl acetate (3×200 ml). The extracts were combined and extracted with 0.4N-HCl (250 ml). The aqueous extract was washed with ethyl acetate (200 ml), basified with 2N-NaOH, and extracted with chloroform (3×200 ml). The organic extracts were dried (MgSO₄) and evaporated in vacuo to give a solid which was recrystallised from methanol-ethyl acetate to yield the product free base (3.14 g).

The dihydrochloride salt of the product was prepared in methanol with etheral hydrogen chloride as colourless crystals. (Found: C,51.55; H,6.6; N,7.2 $C_{16}H_{18}N_2O.2HCl$. $2.5H_2O$ requires C,51.6; H,6.8; N,7.5%).

EXAMPLE 11

Endo-(phenanthrin-6-yloxy)-8-methyl-8-azabicyclo[3.2.1]octane

The title compound was prepared by the procedure given in Example 10 using 6-chlorophenanthrine (4.63g, 21.7 mmol), tropine (2.78g, 19.7 mmol), and sodium hydride, 80% dispersion in oil (0.65g, 21.7 mmol) in dimethyl sulphoxide (100 ml). The crude product was purified by chromatography (alumina; ether). The dihydrochloride salt was prepared with ethereal hydrogen chloride and methanol as pale yellow crystals (2.55g), m.p. 215°-235° (dec) (Found: C, 62.3; H, 6.45; N, 6.8 $C_{21}H_{22}N_2O2HCl$ ⅓ $H_2O$ requires C, 62.3; H, 6.35; N,6.9%).

EXAMPLE 12

Endo-3-(benzoxazol-2-yloxy)-8-methyl-8-azabicyclo[3.2.1]octane

A stirred solution of tropine (3.02 g, 21.4 mmol) in dry tetrahydrofuran (40 ml) was treated dropwise with 1.48M-butyllithium in hexane (14.5 ml) under an atmosphere of nitrogen. After the slight exotherm had subsided, 2-chlorobenzoxazole (2.5 ml, 21.9 mmol) was added dropwise so that the temperature remained below 30°. After 1 h, the solution was evaporated in vacuo and the residue treated with chloroform (150 ml). The mixture was filtered and the filtrate evaporated in vacuo to give a yellow oil. The oil was purified by chromatography (alumina;ether) to give the product as colourless crystals (4.00 g) m.p. 85°-87° (Found: C, 69.5; H, 7.1; N, 10.9. $C_{15}H_{18}N_2O_2$ requires C, 69.7; H.7.0; N, 10.8%)

EXAMPLE 13

Endo-methyl-3-(3-methyl-5,6-cyclohexenopyridin-2-yloxy)-8-azabicyclo[3.2.1]octane This compound was prepared by the procedure given in 33.6 mmol), and sodium hydride, 80% dispersion in oil (1.11 g, 37 mmol) in dimethyl sulphoxide (100 ml). The crude product was purified by chromatography (alumina; di-iso-propyl ether) to give the product as a light yellow solid (0.97 g,) m.p. 51°-57°.

EXAMPLE 14

Endo-2-(8-methyl-8-azabicyclo[3.2.1]octan-3-yloxy)-5,6-cycloheptenopyridine-3-carboxylic acid ethyl ester This compound was prepared by the procedure given in Example 10 using 2-bromo-5,6-cycloheptenopyridine-3-carboxylic acid ethyl ester (9.93 g, 33.3 mmol), tropine (4.28 g, 30.3 mmol), and sodium hydride, 80% dispersion in oil (1 g, 33.3 mmol) in dimethyl sulphoxide (100 ml). The crude product was purified by chromatography (alumina; ether) to give a colourless oil. The monohydrochloride salt of the product was prepared in methanol with ethereal hydrogen chloride and recrystallised from propan-2-ol- to give white crystals (0.59 g), m.p. 234°-239° (dec).

I claim:

1. A pyrazinyl or pyridazinyl compound of the formula

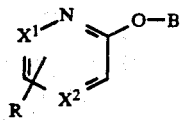 (Ia)

wherein
either $X^1$ is N and $X^2$ is CH or $X^1$ is CH and $X^2$ is N
R is hydrogen, $C_{1-4}$alkyl, $C_{1-4}$alkoxy, amino, mono-$C_{1-4}$alkylamino, di($C_{1-4}$alkyl)amino, fluorine, chlorine, trifluoromethyl, phenyl, mono-chloro- or fluorophenyl, $C_{1-4}$alkylphenyl, mono-$C_{1-4}$-alkoxyphenyl, carboxy, carboxamido, nitro, thiol, $C_{1-4}$-alkylthio, or $C_{1-4}$-alkoxycarbonyl;
with the proviso that R is not hydrogen when $X^1$ is N and $X^2$ is CH; and
B is

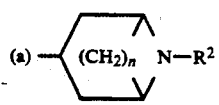 (II)

where n is 2, 3 or 4 and $R^2$ is hydrogen, $C_{1-4}$alkyl, $C_{1-4}$alkoxy, allyl, methallyl, cyclopentyl, cyclohexyl, cyclopentylmethyl, cyclohexylmethyl or benzyl,

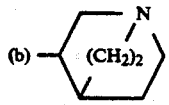 (III)

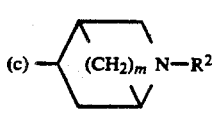 (IV)

where $R^2$ has the meaning given above and m is 1, 2 or 3 or

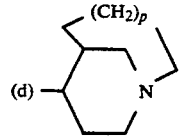 (V)

where p is 0, 1 or 2,
or a N-oxide of a pyrazinyl or pyridazinyl nitrogen thereof, or a pharmaceutically acceptable acid addition salt of a compound of formula I2 or of said N-oxide thereof.

2. A compound of claim 1 wherein R is hydrogen.
3. A compound of claim 1 wherein $R^2$ is $C_{1-4}$alkyl.
4. A compound of claim 1 in which B is formula II wherein n is 2 and $R^2$ is methyl.
5. A compound of claim 1 in which B is formula IV wherein m is 2 and $R^2$ is methyl.
6. A compound of formula 1 in which B is formula V wherein p is 1.
7. A compound as claimed in claim 1 which is endo-8-methyl-3-(2-pyrazinyloxy)-8-azabicyclo[3.2.1]octane or a pharmaceutically acceptable salt thereof.
8. A compound as claimed in claim 1 which is endo-3-(6-chloropyridiazin-2-yloxy)-8-methyl-8-azabicyclo[3.2.1]octane or a pharmaceutically acceptable salt thereof.
9. A compound as claimed in claim 1 which is endo-3-(6-chloropyrazin-2-yloxy)-8-methyl-8-azabicyclo[3.2.1]octane or a pharmaceutically acceptable salt thereof.
10. A pharmaceutical composition comprising a compound of claim 1, or a N-oxide of a pyrazinyl or pyridazinyl nitrogen thereof, or a pharmaceutically acceptable acid addition. salt of such compound or such N-oxide thereof, in association with a pharmaceutically acceptable carrier.
11. A method of antagonizing 5-HT$_3$ receptors in warm blooded animals in need thereof comprising administering to such animal an amount effective to antagonize 5-HT$_3$ receptors of a compound of the formula IA

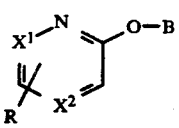 (Ia)

wherein
either $X^1$ is N and $X^2$ is CH or $X^1$ is CH and $X^2$ is N
R is hydrogen, $C_{1-4}$alkyl, $C_{1-4}$alkoxy, amino, mono-$C_{1-4}$alkylamino, di($C_{1-4}$alkyl)amino, fluorine, chlorine, trifluoromethyl, phenyl, mono-chloro- or fluorophenyl, $C_{1-4}$alkylphenyl, mono-$C_{1-4}$-alkoxyphenyl, carboxy, carboxamido, nitro, thiol, $C_{1-4}$-alkylthio, or $C_{1-4}$-alkoxycarbonyl;
with the proviso that R is not hydrogen when $X^1$ is N and $X^2$ is CH; and
B is

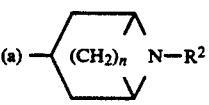 (II)

where n is 2, 3 or 4 and $R^2$ is hydrogen, $C_{1-4}$alkyl, $C_{1-4}$alkoxy, allyl, methallyl, cyclopentyl, cyclohexyl, cyclopentylmethyl, cyclohexylmethyl or benzyl,

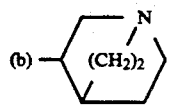 (III)

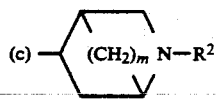 (IV)

where $R^2$ has the meaning given above and m is 1, 2 or 3 or

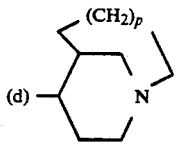 (V)

where p is 0, 1 or 2,
or a N-oxide of a pyrazinyl or pyridazinyl nitrogen thereof, or a pharmaceutically acceptable acid addition salt of a compound of formula Ia or of said N-oxide thereof.

12. A method of claim 8 in which the compound of formula 1A is selected from
endo-8-methyl-3-(2-pyrazinyloxy)-8-azabicyclo[3.2.1]-octane;
endo-3-(6-chloropyridazin-2-yloxy)-8-methyl-8-azabicyclo[3.2.1]octane; and
endo-3-(6-chloropyrazin-2-yloxy)-8-methyl-8-azabicyclo[3.2.1]octane, or a pharmaceutically acceptable salt thereof.

* * * * *